United States Patent [19]

Rys et al.

[11] Patent Number: 4,954,282

[45] Date of Patent: Sep. 4, 1990

[54] ACYL ISETHIONATE SKIN CLEANSING COMPOSITIONS

[75] Inventors: Karla J. Rys, Little Ferry; Alan P. Greene, Flemington; Frederick S. Osmer, Parsippany, all of N.J.; Joseph J. Podgorsky, Slate Hill, N.Y.

[73] Assignee: Lever Brothers Company, New York, N.Y.

[21] Appl. No.: 340,185

[22] Filed: Apr. 19, 1989

[51] Int. Cl.$^5$ ............................ C11D 9/32; C11D 1/28
[52] U.S. Cl. ................................. 252/117; 252/121; 252/545; 252/557; 252/DIG. 16
[58] Field of Search ............... 252/557, 545, DIG. 16, 252/117, 121

[56] References Cited

U.S. PATENT DOCUMENTS

| | | | |
|---|---|---|---|
| 2,894,912 | 7/1959 | Geitz | 252/121 |
| 3,879,309 | 4/1975 | Gatti et al. | 252/117 |
| 4,007,125 | 2/1977 | Prince | 252/117 |
| 4,206,069 | 6/1980 | Borrello | 252/122 |
| 4,211,675 | 7/1980 | Machin | 252/557 |
| 4,231,904 | 11/1980 | Machin | 252/557 |
| 4,335,025 | 6/1982 | Barker et al. | 252/550 |

FOREIGN PATENT DOCUMENTS 2402223 7/1974 Fed. Rep. of Germany .
2813324 10/1978 Fed. Rep. of Germany .

*Primary Examiner*—Prince E. Willis
*Attorney, Agent, or Firm*—Milton L. Honig

[57] ABSTRACT

A skin cleansing composition is provided that includes a combination of $C_{16}$–$C_{18}$ acyl isethionate ester salts having no more than 25% $C_{14}$ or lower acyl groups with at least one co-active surfactant. The weight ratio of acyl isethionate to co-active will range from about 20:1 to about 1:1. Soap is present in an amount no higher than 10% by weight of the composition.

4 Claims, No Drawings

ACYL ISETHIONATE SKIN CLEANSING COMPOSITIONS

BACKGROUND OF THE INVENTION

1. Field of the Invention

The invention relates to skin cleansing compositions containing major amounts of acyl isethionates and exhibiting improved skin mildness.

2. The Prior Art

Traditionally, soap has been utilized as a skin cleanser. Soap is, however, a very harsh chemical. Irritated and cracked skin result from use of soap, especially in colder climates. Of course, there are certain benefits from soap including that of low cost, easy manufacture into bars, and good lathering qualities.

There has been much commercial activity to replace soaps with milder surfactants. Particularly successful has been the introduction of syndet mild toilet bars, especially those based on sodium cocoyl isethionates. Patents relating to this technology include U.S. Pat No. 2,894,912 (Geitz) disclosing a detergent bar containing 30–70% $C_6$–$C_{18}$ acyl esters of isethionic acid, a suds-boosting detergent salt such as 2–10% alkyl sulfate and 2.5–25% soap.

U.S. Pat. No. 4,007,125 (Prince) suggests that greater than 75% of the isethionate ester be in the $C_{12}$–$C_{18}$ acyl range. the other hand, U.S. Pat. No. 3,879,309 (Gatti et al.) notes that superior lathering may be achieved by use of lower chain length fatty residues. The patent suggests a mixture of isethionate esters with a fatty acyl distribution of about 28–37% $C_{10}$, about 18–24% $C_{12}$, about 16–21% $C_{14}$, about 9–20% $C_{16}$, and about 10.17% $C_{18}$ chain lengths.

U.S. Pat. No. 4,206,069 (Borrello) obtains transparent toilet bars by combining surfactants among which are the oleic ester of isethionic acid and the $C_8$–$C_{24}$ alkyl ether sulfates having 1–20 ethylene oxide units.

U.S. Pat. No. 4,335,025 (Barker et al.) reports combinations of 4–20% $C_{10}$–$C_{16}$ acyl isethionate with, among others, 18–35% $C_8$–$C_{16}$ alkyl sulfosuccinate.

The present invention seeks compositions with even better skin mildness than those aforementioned while also improving upon lather, mush and processing properties.

Thus, it is an object of this invention to provide a skin cleansing composition based upon acyl isethionates as the main actives but substantially milder to the skin than such previously known compositions.

These and other objects of the invention will become more readily apparent through the following summary and detailed description.

SUMMARY OF THE INVENTION

A skin cleansing composition is provided comprising:
(i) acyl esters of isethionic acid salts, said esters being $C_{16}$–$C_{18}$ acyl isethionates and having no more than 25% $C_{14}$ or lower acyl groups; and
(ii) at least one co-active surfactant;
wherein the weight ratio of said acyl esters to co-active ranges from about 20:1 to about 1:1, and soap is present in an amount from 0 to 10% by weight of the composition.

DETAILED DESCRIPTION OF THE INVENTION

Manipulation of the fatty chain length distribution in isethionate ester salts has been found to achieve significant changes in physical properties of the composition. What the present invention has found is that $C_{16}$–$C_{18}$ isethionate ester salts can act as solid structurants entrapping a liquid co-active. Combination of the two surfactant types provides a mixture that is both better lathering and also milder than either material alone.

The isethionate ester salts employed herein are those of higher chain length fatty acids, those in the range of $C_{16}$–$C_{18}$ acyl, preferably those containing greater than 75% $C_{16}$–$C_{18}$ acyl residues. There should be avoided any substantial amount of the lower fatty acid residues; for instance, there should be no more than about 25% $C_{14}$ or lower acyl groups, preferably no more than 10% optimally no more than 5%. Isethionate esters of the tallow $C_{16}$–$C_{18}$ variety are much milder than those of the $C_{12}$–$C_{14}$ coco variety. Use of $C_{16}$–$C_{18}$ acyl isethionate salts does, however, present a problem with lathering properties. This problem may be ameliorated by inclusion of one or more appropriate co-actives.

A number of anionic, nonionic, cationic and amphoteric surfactants may be employed as the co-active. Among suitable anionic co-actives are the alkyl ether sulfates, alkyl ether sulfonates, sarcosinates, sulfosuccinates, taurates and combinations thereof. Among suitable amphoteric co-actives may be included alkylbetaines, amidopropyl betaines, amidopropyl sultaines and combinations thereof.

The relative amounts of modified isethionate esters to co-actives will range in the weight ratio of about 20:1 to about 1:1, preferably from about 5:1 to about 2:1, optimally about 3:1.

Alkyl ether sulfates of the present invention will be of the general formula $R-O(CH_2CH_2)_nOSO_3^- M^+$ wherein R ranges from $C_8$–$C_{20}$ alkyl, preferably $C_{12}$–$C_{15}$ alkyl, n is an integer from 9 to 40, preferably from 10 to 20, optimally about 12, and $M^+$ is a sodium, potassium, ammonium or triethanolammonium cation. Typical commercial co-actives of this variety are listed in the Table below.

| Trademark | Chemical Name | Physical Form | Manufacturer |
| --- | --- | --- | --- |
| Alkasurf ES-60 | Sodium Laureth Sulfate | Paste | Alkaril |
| Cycloryl TD | TEA Laureth Sulfate | Paste | Cyclo |
| Standapol 125-E | Sodium Laureth-12 Sulfate | Liquid | Henkel |
| Cedepal TD407MF | Sodium Trideceth Sulfate | Paste | Miranol |

Alkyl ether sulfonates may also be employed for the present invention. Illustrative of this category is a commercial product known as Avenel S-150 commonly known as a sodium $C_{12}$–$C_{15}$ Pareth-15 sulfonate.

Another co-active type suitable for use in the present invention is that of the sulfosuccinates. This category is best represented by the monoalkyl sulfosuccinates having the formula: $RO_2CCH_2CH(SO_3^-Na^+)COO^-M^+$; and amido-MEA sulfosuccinates of the formula: $RCONHCH_2CH_2O_2CCH_2CH(SO_3^{-M+})COO^-M^+$; wherein R ranges from $C_8$–$C_{20}$ alkyl, preferably $C_{12}$–$C_{15}$ alkyl and $M^+$ is a sodium, potassium, ammonium or triethanolammonium cation. Typical commercial products representative of these co-actives are those listed in the Table below.

| Trademark | Chemical Name | Physical Form | Manufacturer |
| --- | --- | --- | --- |
| Emcol 4400-1 | Disodium Lauryl Sulfosuccinate | Solid | Witco |
| Schercopol CMSNa | Disodium Cocoamido MEA Sulfosuccinate | Liquid | Scher |
| Emcol 4100M | Disodium Myristamido MEA Sulfosuccinate | Paste | Witco |
| Schercopol | Disodium Oleamido MEA | Liquid | Scher |
| Varsulf S1333 | Disodium Ricinoleamido MEA Sulfosuccinate | Solid | Sherex |

Sarcosinates may also be useful in the present invention as a co-active. This category is indicated by the general formula $RCON(CH_3)CH_2CO_2^{13}M^+$, wherein R ranges from $C_8-C_{20}$ alkyl, preferably $C_{12}-C_{15}$ alkyl and $M^+$ is a sodium, potassium, ammonium or triethanolammonium cation. Typical commercial products representative of these co-actives are those listed in the Table below.

| Trademark | Chemical Name | Physical Form | Manufacturer |
| --- | --- | --- | --- |
| Hamposyl L-95 | Sodium Lauroyl Sarcosinate | Solid | W. R. Grace |
| Hamposyl TOC-30 | TEA Cocoyl Sarcosinate | Liquid | W. R. Grace |

Taurates may also be employed in the present invention as co-actives. These materials are generally identified by the formula $RCONR'CH_2CH_2SO_3^-M^+$, wherein R ranges from $C_8-C_{20}$ alkyl, preferably $C_{12}-C_{15}$ alkyl, R' ranges from $C_1-C_4$ alkyl, and $M^+$ is a sodium, potassium, ammonium or triethanolammonium cation. Typical commercial products representative of these co-actives are those listed in the Table below.

| Trademark | Chemical Name | Physical Form | Manufacturer |
| --- | --- | --- | --- |
| Igepon TC 42 | Sodium Methyl Cocoyl Taurate | Paste | GAF |
| Igepon T-77 | Sodium Methyl Oleoyl Taurate | Paste | GAF |

Within the category of amphoterics there are three general categories suitable for the present invention. These include alkylbetaines of the formula $RN^+(CH_3)_2CH_2CO_2^-M^+$, amidopropylbetaines of the formula $RCONHCH_2CH_2CH_2N^+(CH_3)_2CH_2CO_2^-M^+$, and amidopropyl sultaines of the formula $RCONHCH_2CH_2N^+(CH_3)_2CH_2SO_3^-M^+$, wherein R ranges from $C_8-C_{20}$ alkyl, preferably $C_{12}-C_{15}$ alkyl, and M is a sodium, potassium, ammonium or triethanolammonium cation. Typical commercial products representative of these co-actives are found in the Table below.

| Trademark | Chemical Name | Physical Form | Manufacturer |
| --- | --- | --- | --- |
| Lonzaine C | Cocamidopropyl Betaine | Liquid | Lonza |
| Lonzaine CS | Cocamidopropyl Hydroxysultaine | Liquid | Lonza |
| Lonzaine 12C | Coco-Betaine | Liquid | Lonza |
| Schercotaine MAB | Myristamidopropyl Betaine | Liquid | Lonza |

-continued

| Trademark | Chemical Name | Physical Form | Manufacturer |
| --- | --- | --- | --- |
| Velvetex OLB-50 | Oleyl Betaine | Paste | Henkel |

Within the broad category of liquid co-actives, the most effective are the alkyl ether sulfates, alkyl ether sulfonates and sulfosuccinates.

As previously noted, soap is a very harsh chemical and when present in the compositions of this invention should be at a level no higher than 10%, preferably less than 5%, and advantageously totally absent.

Free fatty acids of 8-22 carbon atoms are desirably incorporated within the compositions of the present invention. Some of these fatty acids are present to operate as superfatting agents and others as skin feel and creaminess enhancers. Superfatting agents enhance lathering properties and may be selected from fatty acids of carbon atoms numbering 8-18, preferably 10-16, in an amount up to 40% by weight of the composition. Skin feel and creaminess enhancers, the most important of which is stearic acid, are also desirably present in these compositions.

Other performance chemicals and adjuncts may be needed with these compositions. The amount of these chemicals and adjuncts may range from about 1% to about 40% by weight of the total composition. For instance, there may be required anti-wear agents such as polycarboxylate polymers, thickeners such as Polymer JR ® and natural gums, humectants such as glycerine, germicides, perfumes, colorants, pigments such as titanium dioxide, electrolytes, and water.

Evaluation of an active's skin mildness properties were determined through one or both of the following test procedures.

The Patch Test

This test is employed to screen formulations for the more extensive Flex Wash. In a Patch Test, up to six formulations can be tested at the same time on each subject, using occluded patches which remain on the forearm for 24 hours. Test sites are evaluated at 4 and 24 hours following the removal of the patches for erythema and dryness. Evaluation scores range from 0 for no response to 20 (moderate) with five point increments.

The Flex Wash Test

The Flex Wash procedure consists of four daily 60 second washes of the antecubital fossa (flex area of elbow). This method was designed to produce erythema quickly. Erythermal response varies only slightly with temperature and humidity fluctuations making the protocol suitable for year round testing.

Approximately 15 panelists were used as the test population. Panelist flex areas must be free of any skin condition (eczema, dryness, irritation, cuts or abrasions). Anyone taking antihistamines, anti-inflammatory drugs (more than 8 per week) or topical, oral or injectable cortisone on a regular basis was excluded from the study. The panel was divided into two subgroups which were balanced for left handedness. Group I was assigned composition "A" for the left flex and "B" for the right flex. Group II reversed the order.

Following an evaluation, the panelist was instructed to moisten the left flex area. Sponge and test compositions formulated as toilet bars were dampened with tap water (100 ppm calcium/magnesium ions). The sponge was then stroked over the test bar 10 times by the evaluator. The "dosed" sponge was placed in panelist's right hand. Panelist then washed the left flex area for exactly 60 seconds (approximately 120 strokes). Thereupon, the flex was rinsed and patted dry. This washing procedure was repeated on the right arm with the appropriate composition. Washing by this procedure was repeated 4 times daily for 5 consecutive days or a total of 19 washes. Treatment times were scheduled prior to washing and 4 hours after the third daily wash.

One trained assessor evaluated test sites prior to each wash and 4 hours after the third wash of the fifth day for a total of 20 evaluations. The grading scale was as follows:

0 - no erythema
0.5 - barely perceptible erythema
1 - mild spotty erythema/no edema
1.5 - mild/moderate erythema/with or without edema
2 - moderate confluent erythema/with or without edema or vesiculation Each site was treated in the prescribed method until a grading of "2" or greater was attained or 19 washings had been completed. When a score of "2" or greater was attained the treatment was discontinued on that flex. The final score was then carried through for all remaining evaluations. The remaining flex was washed until either a grading of at least "2" or 19 treatments were attained, whichever was first. In the Examples of this specification, the final grading is the sum total of grade scores for 20 assessments per panelist averaged over the scores from all panelists. Thus, theoretically the average score could range from 0 to 38; the lower value indicating absolutely no skin irritation while the latter being severe. In practice, scores generally range from 15 to 30.

The following examples will more fully illustrate the embodiments of this invention. All parts, percentages and proportions referred to herein and in the appended claims are by weight of the total composition unless otherwise stated.

EXAMPLE 1

This Example illustrates the difference in mildness between stearoyl and cocoyl isethionate ester salts. Table I lists the various compositions and their Patch Test scores.

TABLE I

| | Formulations and Patch Test Scores | | | | |
|---|---|---|---|---|---|
| Coco/Stearic Ratio | A 100/0 | B 75/25 | C 25/75 | D 0/100 | Dove ® |
| Cocoyl Isethionate** | 40.00 | 28.75 | 8.80 | — | |
| Stearoyl Isethionate*** | — | 11.25 | 31.20 | 40.00 | |
| Stearic Acid | 36.00 | 36.00 | 36.00 | 36.00 | |
| Sodium Isethionate | 11.00 | 11.00 | 11.00 | 11.00 | |
| Water | 10.00 | 10.00 | 10.00 | 10.00 | |
| Salt | 0.35 | 0.35 | 0.35 | 0.35 | |
| Titanium Dioxide | 0.20 | 0.20 | 0.20 | 0.20 | |
| Perfume | 1.00 | 1.00 | 1.00 | 1.00 | |
| Miscellaneous | 1.45 | 1.45 | 1.45 | 1.45 | |
| Patch Score (24 hours) | 10.4 | 8.5 | 6.2 | 1.9* | 6.9 |

*significantly milder than Dove ®
**$C_8 = 7\%$; $C_{10} = 6\%$; $C_{12} = 49\%$; $C_{14} = 19\%$; $C_{16} = 9\%$; $C_{18} = 7\%$
***$C_{14} = 3\%$; $C_{16} = 50\%$; $C_{18} = 47\%$ From the results of Table I, it is evident that as the amount of stearoyl ester increases relative to that of the cocoyl, the compositions become progressively milder. Thus, mildness increases in the order A<B<C<D. Based upon the foregoing results, bar formulation D was submitted for Flex Wash testing to verify the result. Table II lists the Flex Wash outcome which confirms the significantly milder behavior of bar D than that of the commercially well-known Dove ® bar whose major ingredient is sodium cocoyl isethionate.

TABLE II

| | Flex Wash Test | |
|---|---|---|
| Sample | Mean Scores* Endpoint Erythema | Mean Rank Scores Erythema |
| Dove ® | 1.500 | 21.47 |
| D | 0.567 | 9.53 |
| Statistical Analysis | | |
| Rank Scores: (Wilcoxon 2 sample) | P = 0.0001 | |

*Mean end point scores are the mean of the evaluation scores at which the first arm received a grade "2" or greater erythema score or at the completion of nineteen washes.

EXAMPLE 2

A series of physical property evaluations were conducted on the acyl isethionate salts of varying chain length reported in Example 1. Among the further properties measured were that of wear rate, mush and lather. A brief description of the wear rate and mush tests is provided below.

Wear Rate - Pre-weighed bars were washed (rotated 20 times) and placed in a wet soap dish. This procedure was repeated 5 times over a period of two days. After the final wash, the bars were allowed to dry and were then reweighed. Wear rate (g/wash) = Initial Wt. - Final Wt./5.

Mush - Pre-weighed bars were immersed in water for 2 hours. The increase in weight was noted. Mush was removed and the remainder of the bar was dried. After reweighing, mush was calculated as the weight of mush per $cm^2$ of surface mushed. Lower values indicated better performance.

TABLE III

| | Bar Properties With Varying Chain Length Isethionates | | | | | |
|---|---|---|---|---|---|---|
| Bar No. | Coco/Stearic Isethionate Rate | Wear Rate | Mush | Lather 75° F. | 95° F. | 105° F. |
| A | 100/0 | 3.71 | 6.72 | 65 | 80 | 80 |
| B | 75/25 | 1.81 | 6.75 | 15 | 55 | 55 |
| C | 25/75 | 1.56 | 5.55 | 0 | 0 | 0 |
| D | 0/100 | 0.41 | 1.06 | 0 | 0 | 0 |
| E | 50/50 | 1.54 | 9.03 | 5 | 25 | 35 |

From the results of Table III it is evident that the stearoyl isethionate bar (D) has significant advantages in terms of wear and mush relative to that containing cocoyl isethionate. There is, however, a problem with lather, this problem is overcome by use of co-actives as will be seen in Tables IV-VI.

EXAMPLE 3

A number of co-actives were evaluated in the base formulation of Example 1 (D) wherein the isethionate ester was that of stearoyl. Tables IV-VI outline the compositions and Patch Test Scores.

TABLE IV

| Bar No. | Patch Test Scores | | | | | Dove ® |
|---|---|---|---|---|---|---|
| | 1 | 2 | 3 | 4 | 5 | |
| Stearoyl Isethionate** | 33.10 | 33.10 | 33.10 | 33.10 | 40.00 | |
| Stearic Acid | 29.80 | 29.80 | 29.80 | 29.80 | 36.00 | |
| Sodium Isethionate | 9.10 | 9.10 | 9.10 | 9.10 | 11.00 | |
| Water | 10.00 | 10.00 | 10.00 | 10.00 | 10.00 | |
| Disodium Cocamido MEA Sulfosuccinate | — | 15.00 | — | — | — | |
| Disodium Oleamide MEA Sulfosuccinate | — | — | — | 15.00 | — | |
| Sodium C12-15 Pareth-15 Sulfonate | — | — | 15.00 | — | — | |
| Sodium Methyl Cocoyl Taurate | 15.00 | — | — | — | — | |
| Salt | 0.35 | 0.35 | 0.35 | 0.35 | 0.35 | |
| Titanium Dioxide | 0.20 | 0.20 | 0.20 | 0.20 | 0.20 | |
| Perfume | 1.00 | 1.00 | 1.00 | 1.00 | 1.00 | |
| Miscellaneous | 1.45 | 1.45 | 1.45 | 1.45 | 1.45 | |
| Patch Score (24 hrs) | 3.6 | 1.4* | 1.4* | 1.1* | 1.8* | 4.6 |

*significantly milder than Dove ®
**$C_{14}$ = 3%; $C_{16}$ = 50%; $C_{18}$ = 47%

TABLE V

| Bar No. | Patch Test Scores | | | | | Dove ® |
|---|---|---|---|---|---|---|
| | 6 | 7 | 8 | 9 | 10 | |
| Stearoyl Isethionate** | 33.10 | 33.10 | 33.10 | 33.10 | 40.00 | |
| Stearic Acid | 29.80 | 29.80 | 29.80 | 29.80 | 36.00 | |
| Sodium Isethionate | 9.10 | 9.10 | 9.10 | 9.10 | 11.00 | |
| Water | 10.00 | 10.00 | 10.00 | 10.00 | 10.00 | |
| Sodium Lauroyl Sarcosinate | 15.00 | — | — | — | — | |
| TEA Cocoyl Sarcosinate | — | 15.00 | — | — | — | |
| Disodium Ricinoleamide MEA Sulfosuccinate | — | — | 15.00 | — | — | |
| Sodium Methyl Oleoyl Taurate | — | — | — | 15.00 | — | |
| Salt | 0.35 | 0.35 | 0.35 | 0.35 | 0.35 | |
| Titanium Dioxide | 0.20 | 0.20 | 0.20 | 0.20 | 0.20 | |
| Perfume | 1.00 | 1.00 | 1.00 | 1.00 | 1.00 | |
| Miscellaneous | 1.45 | 1.45 | 1.45 | 1.45 | 1.45 | |
| Patch Score (24 hrs) | 6.7 | 5.7 | 1.0* | 4.3 | 1.3* | 6.7 |

*significantly milder than Dove ®
**$C_{14}$ = 3%; $C_{16}$ = 50%; $C_{18}$ = 47%

TABLE VI

| Bar No. | Patch Test Scores | | | | Dove ® |
|---|---|---|---|---|---|
| | 11 | 12 | 13 | 14 | |
| Stearoyl Isethionate** | 33.10 | 33.10 | 33.10 | 40.00 | |
| Stearic Acid | 29.80 | 29.80 | 29.80 | 36.00 | |
| Sodium Isethionate | 9.10 | 9.10 | 9.10 | 11.00 | |
| Water | 10.00 | 10.00 | 10.00 | 10.00 | |
| Sodium Lauroyl Sulfate | 15.00 | — | — | — | |
| Sodium Trideceth Sulfate | — | 15.00 | — | — | |
| Ammonium Myreth Sulfate | — | — | 15.00 | — | |
| Salt | 0.35 | 0.35 | 0.35 | 0.35 | |
| Titanium Dioxide | 0.20 | 0.20 | 0.20 | 0.20 | |
| Perfume | 1.00 | 1.00 | 1.00 | 1.00 | |
| Miscellaneous | 1.45 | 1.45 | 1.45 | 1.45 | |
| Patch Score (24 hrs) | 10.4 | 8.5 | 6.2 | 1.9* | 6.9 |

*significantly milder than Dove ®
**$C_{14}$ = 3%; $C_{16}$ = 50%; $C_{18}$ = 47%

Within each of the three Patch Test series (Tables IV–VI) a base formulation of stearoyl isethionate without co-active was included as well as a standard Dove ® control. In each Patch Test at least one of the co-active bars was significantly milder than Dove ®. Several of the co-active bars were also directionally milder than the control stearoyl isethionate bar.

The test results indicate that the use of taurates, sarcosinates and sulfated ethoxylated alcohols as co-actives result in bars equal in mildness to Dove ®. A combination of sodium $C_{12}$–$C_{15}$ pareth-12 sulfonate (an ethoxylated sulfonated fatty alcohol) and stearoyl isethionate results in a bar significantly milder than Dove ®. Each of the amido-MEA sulfosuccinate/stearoyl isethionate bars were noted to be significantly milder than Dove ®. The alkyl sulfosuccinate/stearoyl isethionate bar was only equivalent to that of Dove ®.

Each of the bars which were shown to be significantly milder than Dove ® in the Patch Test were subjected to a Flex Wash. The Flex Wash was conducted to verify the statistically significant results of the Patch Test. In every case, these results were in agreement and are presented to Table VII below.

TABLE VII

| | Flex Wash Scores | |
|---|---|---|
| | Mean Rank Score | Mean Endpoint Erythema |
| Dove ® | 23.50 | 1.688 |
| Sodium $C_{12}$–$C_{15}$ Pareth-12 Sulfonate | 9.5 | 0.688 |
| Dove ® | 17.62 | 1.308 |
| Disodium Ricinoleamido MEA-Sulfosuccinate | 9.38 | 0.731 |
| Dove ® | 16.92 | 1.192 |
| Disodium Cocamido MEA-Sulfosuccinate | 10.08 | 0.615 |

EXAMPLE 4

This Example records the lather properties of bars having various co-actives in combinations with stearoyl isethionate. Bar formulations are listed in Table IV–VI.

The Lather Volume Measurement test involved rotating the experimental bars 15 half turns in a basin containing 105° F. water. The bar was then set aside and the resulting lather was worked for 10 seconds. A measuring funnel was then placed over the hands and both were lowered into a sink filled with water to the 0 ml mark on the measuring funnel. When the hands were fully immersed, they were removed from beneath the funnel. The funnel was then lowered to the bottom of the sink and lather volume was measured.

TABLE VIII

| Bar No. | Co-Active | Lather Volume Measurement Results | | |
|---|---|---|---|---|
| | | 75° F. | 95° F. | 105° F. |
| 1 | Sodium Methyl Cocoyl Taurate | unprocessable | | |
| 2 | Disodium Cocamido MEA Sulfosuccinate | 50 | 80 | 60 |
| 3 | Sodium $C_{12}$–$C_{15}$ Pareth-12 Sulfonate | 0 | 15 | 15 |
| 4 | Disodium Oleamide MEA Sulfosuccinate | 0 | 0 | 0 |
| 6 | Sodium Lauroyl Sarcosinate | 30 | 60 | 70 |
| 7 | TEA Cocoyl Sarcosinate | 0 | 15 | 15 |
| 8 | Disodium Ricinoleamido MEA Sulfosuccinate | 0 | 25 | 25 |
| 9 | Sodium Methyl Oleyl Taurate | 0 | 0 | 0 |
| 11 | Sodium Laureth-12 Sulfate | 0 | 25 | 30 |
| 12 | Sodium Trideceth Sulfate | 30 | 50 | 55 |
| 13 | Ammonium Myreth Sulfate | 45 | 75 | 55 |
| 5,10,14 | No Co-Active Present | 0 | 0 | 0 |

From the results of Table VIII it is evident that sarcosinates significantly increased the lather of the stearoyl isethionate bar, the sodium derivative much more so that the TEA derivative. Activity of the amido-MEA sulfosuccinate decreased with increase in alkyl chain length. Thus, disodium cocamido MEA sulfosuccinate has the best lather, the ricinoleamide analog had modest lather volume, and the oleamido analog did not lather at all. All of the ethoxylated and sulfated/sulfonated alcohols provided an increase in bar lather.

The foregoing description and examples illustrate selected embodiments of the present invention and in light thereof various modifications will be suggested to one skilled in the art, all of which are within the spirit and purview of this invention.

What is claimed is:

1. A skin cleansing composition comprising:
   (i) acyl esters of isethionic acid salts, said esters being $C_{16}$–$C_{18}$ acyl isethionates and having no more than 25% $C_{14}$ or lower acyl groups; and
   (ii) at least one co-active surfactant which is an amido sulfosuccinate;
   wherein the weight ratio of said acyl esters to co-active ranges from about 20:1 to about 1:1, and soap is present in an amount from 0 to 10% by weight of the composition.

2. A composition according to claim 1 wherein the sulfosuccinate is a cocoamido sulfosuccinate.

3. A composition according to claim 1 wherein the ratio of isethionate ester to co-active ranges from 5:1 to 2:1.

4. A composition according to claim 1 wherein soap is absent.

* * * * *